United States Patent
Bragos Bardia et al.

(10) Patent No.: US 7,442,538 B2
(45) Date of Patent: Oct. 28, 2008

(54) MODULAR SYSTEM COMPRISING MULTIPLE AUTOMATED MINI-BIOREACTORS FOR HIGH-THROUGHPUT SCREENING (HTS) IN BIOTECHNOLOGY

(75) Inventors: Ramon Bragos Bardia, Barcelona (ES); Javier Rosell Ferrer, Barcelona (ES); Pere Joan Riu Costa, Barcelona (ES); Francesc Godia Casablancas, Barcelona (ES); Jordi Joan Cairo Badillo, Bellaterra (ES); Carles Paredes Muñoz, Bellaterra (ES); Ferran Rodriguez Omedes, Cerdanyola del Valles (ES)

(73) Assignee: Hexascreen Culture Technologies, S.L., Cerdanyola del Valles (Barcelona)

( * ) Notice: Subject to any disclaimer, the term of this patent is extended or adjusted under 35 U.S.C. 154(b) by 481 days.

(21) Appl. No.: 11/139,145

(22) Filed: May 27, 2005

(65) Prior Publication Data
US 2005/0255587 A1   Nov. 17, 2005

Related U.S. Application Data

(63) Continuation of application No. PCT/ES03/00607, filed on Nov. 27, 2003.

(30) Foreign Application Priority Data
Nov. 28, 2002   (ES) .................... 200202828

(51) Int. Cl.
   *C12N 1/00* (2006.01)
(52) U.S. Cl. .................... 435/243; 435/288.7

(58) Field of Classification Search .................. 435/243, 435/294.1, 288.7
See application file for complete search history.

(56) References Cited

U.S. PATENT DOCUMENTS 5,353,792 A * 10/1994 Lubbers et al. ............. 600/311
5,811,255 A *  9/1998 Hunter et al. ................ 435/29
6,133,021 A * 10/2000 Gu et al. .................... 435/288.7

(Continued)

FOREIGN PATENT DOCUMENTS

DE         19710652         9/1998

(Continued)

OTHER PUBLICATIONS

Gu M.B., Kim B. C., Cho J. and Hansen P.D. The continuous monitoring of field water samples with a novel multi-channel two-stage mini-bioreactor system. 2001. Environmental Monitoring and Assessment, v. 70 p. 71-81.*

(Continued)

*Primary Examiner*—Walter D. Griffin
*Assistant Examiner*—Shanta G Doe
(74) *Attorney, Agent, or Firm*—Peter B. Scull; K Kalan; Berenbaum, Weinshienk & Eason (57) ABSTRACT

The invention relates to a method and a device which are used to obtain and maintain multiple biological cultures, with environmental parameters similar to those of larger bioreactors (from 1 L) and with a degree of measurement automation similar to that currently obtained using microplates (1-2 mL). The aforementioned environmental parameters include at least the following: measurement and control of temperature, agitation and aeration, measurement and control of pH and dissolved oxygen and measurement of the biomass.

20 Claims, 7 Drawing Sheets

U.S. PATENT DOCUMENTS

| | | | |
|---|---|---|---|
| 6,397,689 B1 * | 6/2002 | Moles | 73/863.84 |
| 2002/0025547 A1 * | 2/2002 | Rao | 435/40.5 |
| 2002/0146816 A1 | 10/2002 | Vellinger et al. | |
| 2002/0146818 A1 * | 10/2002 | Downs et al. | 435/294.1 |
| 2003/0147132 A1 * | 8/2003 | Behnsen et al. | 359/368 |

FOREIGN PATENT DOCUMENTS

| | | |
|---|---|---|
| WO | WO 00/44876 | 8/2000 |
| WO | WO 00/45953 A | 8/2000 |
| WO | WO 00/66269 A | 11/2000 |
| WO | WO 02/14539 A | 2/2002 |
| WO | WO 02/083852 A2 | 10/2002 |

OTHER PUBLICATIONS

Fujieda Sh. and Tanaka S. Fuzzy control for the precision water bath of the heat exchange calorimeter.1992.Journal of Thermal Analysis, v. 38, p. 1785-1792.*

PGC Scientific 1995-1996 General Catalog, p. 1-3.*

International Search Report for International Application No. PCT/ES2003/000607, Spanish Patent and Trademark Office (SPTO) acting as International Search Authority, Mar. 2, 2004, 3 pgs.

Antonio De Leon et al., Design, characterization and application of a minibioreactor for the culture of human hematopoietic cells under controlled conditions, Cytotechnology, 1998, pp. 127-138, vol. 28, Kluwer Academic Publishers, The Netherlands.

Yordan Kostov et al., Low-cost Microbioreactor for High-Throughput Bioprocessing, Biotechnology and Bioengineering, 2001, pp. 346-352, vol. 72, No. 3, John Wiley & Sons, Inc.

Michel M. Maharbiz et al., Microbioreactor Arrays with Parametric Control for High-Throughput Experimentation, Biotechnology and Bioengineering, Feb. 20, 2004, pp. 376-381, vol. 85, No. 4, published online in Wiley InterScience.

Frank G. Gao et al., Long-term Continuous Monitoring of Dissolved Oxygen in Cell Culture Medium for Perfused Bioreactors using Optical Oxygen Sensors, Biotechnology and Bioengineering, May 20, 2004, vol. 86, No. 4, published online in Wiley InterScience.

W.H. Baumann et al., Microelectronic Sensor System for Microphysiological Application on Living Cells, Sensors and Actuators, 1999, pp. 1-15, Elsevier Science S.A.

Radleys Discovery Technologies, GreenHouse Parallel Synthesiser, product catalog. 2001, 7 pgs., Radleys Discovery Technologies Ltd., Essex, U.K.

Biotechnology and Cell Culture Products, The Ultra M Micro Bioreactor System; Multiparameter Monitoring System for Organ Perfusion & Bioreactors, product catalog [online], 8 pages.

* cited by examiner

MODULAR SYSTEM COMPRISING MULTIPLE AUTOMATED MINI-BIOREACTORS FOR HIGH-THROUGHPUT SCREENING (HTS) IN BIOTECHNOLOGY

CROSS-REFERENCE TO RELATED APPLICATIONS

The present invention is a continuation of International Patent Application No. PCT/ES2003/000607, entitled "Modular System Comprising Multiple Automated Mini-BioReactors for High-Throughput Screening („HTS) in Biotechnology" and filed Nov. 27, 2003, specifically incorporated herein by reference for all that it discloses and teaches. The International Patent Application No. PCT/ES2003/000607 claimed priority from the prior-filed Spanish Application No. P200203838, filed Nov. 28, 2002.

The present invention relates to a method and a device for obtaining and maintaining multiple biological cultures, with environmental characteristics similar to those of larger bioreactors (from 1 liter) and with a degree of measurement automation similar to that currently obtained with microplates (1-2 ml). The environmental characteristics may include temperature measurement and control, stirring and aeration, ph and dissolved oxygen measurement and control and biomass measurement.

STATE OF THE ART

Development of new or improved organisms, new substances and new processes is being promoted by application of the technology based on the use of genomic and proteomic techniques and combinatorial chemistry. The fields of application of such techniques are as broad as biomedicine, biotechnology, food industry and environment, and without doubt they will be growing in the near future, due to the potential of this technology. One must not forget that many capabilities in the existing organisms are still to discover. In this sense, one will have to face up to the ability to screen, in reasonable time, and with highly technified, automated and standardized means, both the potential of the different cells and natural or modified enzymes and the therapeutic and/or toxic effects of the different molecules developed with said techniques. Systems allowing said screening have been referred to as High Throughput Screening (HTS) systems.

In biotechnology HTS may be dealt at different levels and the existing systems are adapted to each of them according to the specific necessities required by the end user. Therefore, at a molecular level, the interest is focused on permitting multiple assays to be carried out, usually of an enzymatic type, where multiple activities or metabolites are monitored, in different product development stages in biotechnology and more particularly in the field of therapeutic applications. In contrast, at a cellular level, actions are focused on determining, through manual and visual methods, the effect of the product in clinical stages or assays on the effects of several compounds on the cell growth and/or activity.

Technologies currently used in processes for identifying and developing new substances and processes are, on the one hand, small volume culture elements (1-10 ml) which do not allow the in situ control of the process critical variables, and which monitoring through conventional techniques is at the very least capital intensive regarding the amount of time required. Furthermore, due to the small reaction volume, the number of samples which can be extracted is reduced. Implementation of in situ and in-line measuring systems would therefore involve a great step forward in this field.

On the other hand, the use of in-line measuring systems is limited to bioreactors at a laboratory scale (2-5 liters) and larger scales. However, their high purchasing cost, their operation cost (certainly high if one refers to animal cell cultures) as well as the need for certainly specialized labor makes it difficult the use of bioreactor batteries for studying different culture/reaction conditions for each potential product of interest. Then, there is a potential technological gap that combines the bioreactor measuring and controlling capabilities with the scalability of the small reaction/culture systems. It is this gap that the present patent intends to cover.

In the early stages of development of new substances with biological activity or biotechnological processes, determination of parameters such as for example the media dissolved oxygen concentration, pH, temperature or ionic strength is of special interest. Without a clear knowledge of their values and ranges during the assays, reproducing the ambient conditions in which it was created may result very nearly impossible, making it nearly unfeasible passing to subsequent developing stages. The concept appeal in which this device is based upon is that the final process conditions may be determined in the HTS.

One study of the devices existing in the market reveals that the product having a greater similarity with the one presented, with regard to its design and volume, is a device comprising different vials which potential field of application consists of the synthesis of compounds according to combinatorial chemistry schemes. However, its design is not directed to the use of said vials as bioreactors.

Besides the chemical field, in the medical field there also exist products having certain similarities to the one presented, although in this case the similarities are not as designed as functional. Thus, in the hospital field there exist devices based on 1 or 6-well culture plates (culture laboratory typical elements) which are used for maintaining cultures in specified samples of tissue, which is carried out by media continuous perfusion through the culture wells where the tissues are provided. Said plates require, however, a bulky equipment (incubator) for maintaining temperature, moisture and atmospheric composition conditions, and they are devoid of an in-line monitoring system for culture conditions.

SUMMARY OF THE INVENTION

According to a first aspect, the present invention relates to a device for simultaneously and automatedly carrying out a large number of biological cultures at a small volume and with controlled conditions, in such a way that said conditions are similar to those which can be obtained with large scale bioreactors, which is characterized in that it comprises:
  at least one plate made of a plastic material or other transparent material, which comprises a number of mini-bioreactors for culture in sterile conditions, each of them being sealed to the environment, to the rest of the mini-bioreactors and to a common thermostat bath, each mini-bioreactor including an individual stirring member for allowing homogenization of its contents, and sterile access points enabling filling, inoculation, gas exchange, liquid exchange and parameter measurement; and
  a device intended for receiving at least one plate therein, the plates being fitted through the opening of at least one part of said device, said device comprising means for controlled heat exchange with the thermostat bath, means for energy transmission to the individual stirring members, means for gas exchange through sterile filters and means for non-invasive monitoring and/or controlling of the culture parameters.

In one preferred embodiment, each plate further comprises a thermostat bath central stirrer.

Preferably, the plate comprises a number of individual minibioreactors in a polygonal arrangement, with a central area which facilitates common thermostating of said minibioreactors.

The geometrical arrangement of the wells inside the plate ensures, due to their design, that the overall temperature control may be carried out centrally, thus ensuring the thermal homogenization of all the minibioreactors. Multiple plate lateral coupling is allowed by the polygonal shape with the purpose of forming minibioreactor macro-assemblies which would be fitted out by a common device, with individual or group culture parameter variation.

According to one embodiment, the device is connected to a computer system, either via a dedicated connection or through a data communication network.

The system can therefore be indefinitely expanded locally or remotely for achieving the control of a large number of cultures for HTS applications.

In one embodiment, each minibioreactor comprises an upper cover having an optical port comprising a tube that penetrates within the minibioreactor so that its lower end is immersed into a liquid contained in said minibioreactor.

The effect of level variations and condensation on the optical measurements carried out through said optical port is thus avoided.

Optical sensors and light sources may be placed in the optical port at the bottom portion of the plate facing said optical port and/or on the lateral surface of the reservoir.

The purpose of said sensors is measuring absorption, reflection, scattering or fluorescence of the minibioreactor contents.

Optical fibers or light guides may be also placed in the optical port at the bottom portion of the plate facing said optical port and/or on the lateral surface of the reservoir.

The purpose of the optical fibers is remotely measuring absorption, reflection, scattering or fluorescence of the minibioreactor contents.

In one embodiment, an additional port is fitted through the upper cover so that the end of said port is immersed into the liquid, said end being provided with a filter or semi-permeable membrane.

This port allows carrying out measurements related to the minibioreactor contents from its outside and without breaking the sterile barrier.

Other embodiments envisage fitting an additional port through the upper cover so that the end of said port is immersed into the liquid, said end containing sensors or microsensors.

The sensors or microsensors allow carrying out measurements related to the minibioreactor contents from electrical connections made from its outside.

According to one embodiment, the heat exchange between the device and the thermostat bath of the plate is carried out by means of a heating resistance that is in contact with a portion of the plate outer perimeter.

Alternatively, the heat exchange between the device and the thermostat bath of the plate is carried out by means of a Peltier cell that is in contact with a portion of the plate outer surface.

According to a further embodiment, the heat exchange between the device and the thermostat bath of the plate is carried out by means of a heating resistance that is immersed into said bath.

In this case, the resistance would be part of the plate itself.

Other embodiments may envisage that the heat exchange between the device and the bath of the plate is carried out by radio frequency heating performed from the outside.

The device may comprise a temperature probe immersed into the thermostat bath.

The probe allows measuring the temperature in said bath and performing the control thereof.

The device may be further provided with temperature probes immersed into the contents of one or several of the minibioreactors.

The device may be further provided with an additional minibioreactor surrounded, as in the rest of the minibioreactors, by the thermostat bath, into which a temperature probe is immersed.

The probe allows measuring the temperature in the bath, with the advantage that the additional minibioreactor may be different in shape and size to the minibioreactors, and being able not to be sterile.

In one embodiment, the device comprises a stator located below each individual stirring member of the minibioreactor contents for energy transmission to said stirring members.

Alternatively, the device comprises rotating magnets located below each individual stirring member of the minibioreactor contents for energy transmission to said stirring members, said magnets being rotated by a mechanical driving system actuated by a common electric motor. According to a further variant, the magnets are rotated by individual electric motors.

Preferably, the device comprises a stator or a rotating magnet located below the thermostat bath central stirrer for energy transmission to said stirrer.

In one embodiment, the device comprises means for causing the common thermostat bath stirrer to be rotated from drive sequencing to the minibioreactors.

Preferably, each minibioreactor has a volume ranging from 5 to 25 ml.

In one embodiment, the plates are at least in part disposable; they may be formed of a base made of plastic material and at least one cover made of plastic material or other transparent material.

According to a second aspect, the present invention relates to a method for simultaneously and automatedly carrying out a large number of biological cultures at a small volume and with controlled conditions, in such a way that said conditions are similar to those which can be obtained with large scale bioreactors, which is characterized in that it comprises:

carrying out cultures in sterile conditions in a number of minibioreactors provided at least in one plate of plastic material or another transparent material, said minibioreactors being each sealed to the environment, to the rest of the minibioreactors and to a common thermostat bath, and each minibioreactor including an individual stirring member for allowing homogenization of its contents, and sterile access points enabling filling, inoculation, gas exchange, liquid exchange and parameter measurement;

fitting at least one plate into a device which comprises means for controlled heat exchange with the thermostat bath, means for energy transmission to the individual stirring members, means for gas exchange through sterile filters and means for non-invasive monitoring and/or controlling of the culture parameters; and non-invasive monitoring and/or controlling of the culture parameters.

BRIEF DESCRIPTION OF THE DRAWINGS

For a better understanding of what it has been set forth, drawings are accompanied in which, diagrammatically and only by way of a non-limiting example, a specific embodiment of the invention is herein disclosed. In said drawings.

DESCRIPTION OF A PREFERRED EMBODIMENT

The device according to one embodiment of the invention which is shown in the drawings comprises two clearly differentiated parts:

(A) A closed reservoir 1, made of a plastic material (plate, hereinafter), which features may be seen from FIGS. 1a, 1b, 2a and 2b, accommodating a certain number of medium size cells or wells 2 (minibioreactors, hereinafter) (5-25 ml), one of which has been depicted in detail in FIGS. 3a and 3b. The plate 1 may be a single-use plate and, once filled with the culture liquids in a sterile environment, it may be handled and conveyed in a non-sterile environment during the rest of the process.

(B) A measuring device or system 3, shown in FIGS. 5a, 5b, 7a and 7b, accommodating one or more plates 1 therein and providing the common or individual environmental conditions to the minibioreactors 2. The device 3 also provides the measuring systems allowing automatically tracking and controlling of the suitable parameters for each type of biological culture, and respecting the sterile barrier in the plate 1. The device 3 may be replicated indefinitely by means of its connection to a computer network with the purpose of performing, controlling and monitoring a large number of assays, with variation in its reaction/growth conditions and with repetition of conditions in groups of minibioreactors 2 or plates 1, as necessary.

The different parts of the device and its operation are fully described below.

Description of the Plate

Figure 1A:
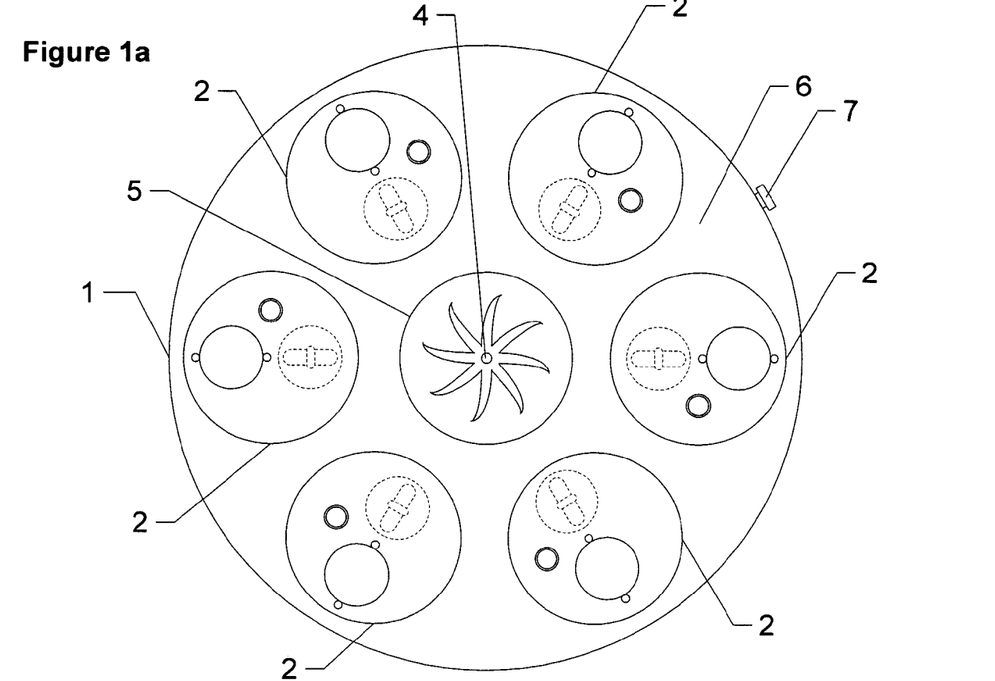
FIGS. 1a and 1b are plan views of respective embodiments of a plate according to the invention containing six minibioreactors, having circular and hexagonal outer profiles, respectively.
Figure 1B:
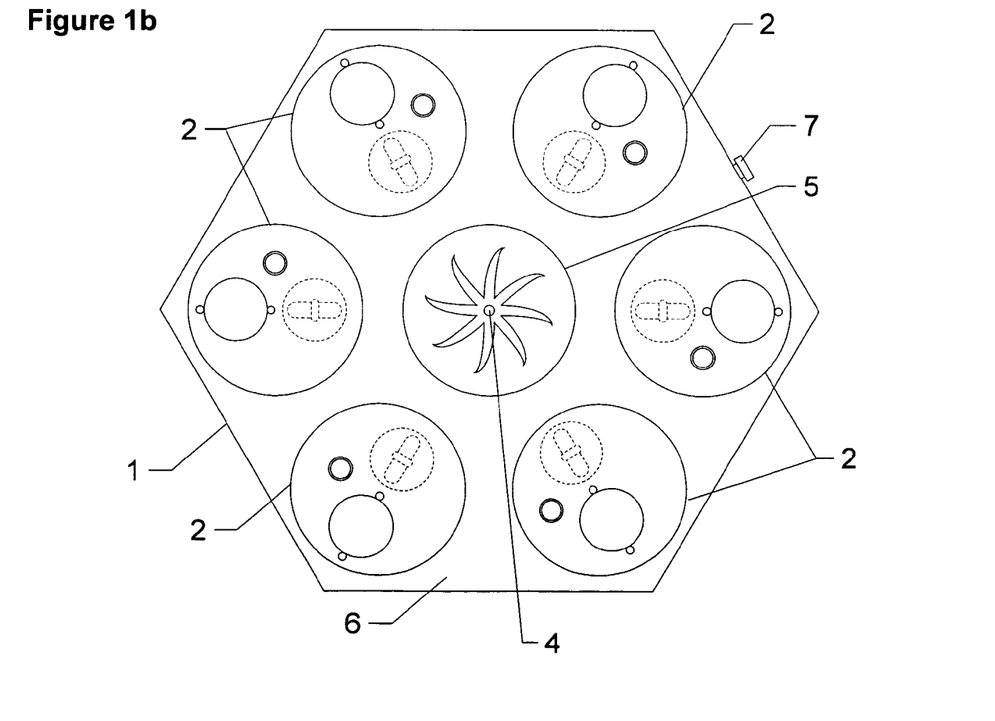

As shown in FIGS. 1a and 1b, a plate 1 may contain six minibioreactors 2 and a central stirring system 4.

The central symmetry of the plate 1 is to be emphasized which allows maintaining the wells 2 at the same temperature with only one central heater 5 heating a common thermostat bath 6, stirred by said stirring system 4. Said bath 6 is filled through a plug 7, which may be also located on an upper cover (not shown).

In FIG. 1a the plate has a circular outer profile, while in the variant of the embodiment shown in FIG. 1b the profile is hexagonal in shape. The perimeter may be of different shapes; the polygonal shape allows several plates 1 to be laterally fitted forming a multiple-well compact assembly 2 (forty-two in the case of six-well hexagonal plates).

Figure 2A:
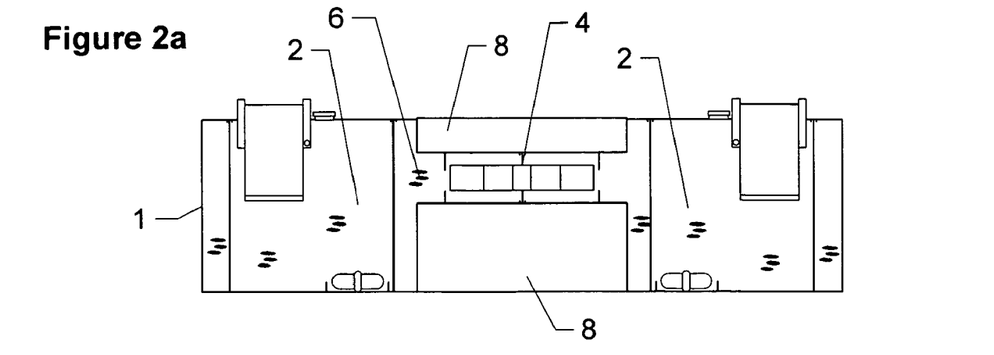
FIGS. 2a and 2b are vertical sectional views of a plate containing six minibioreactors and the central stirring system supported by the structure or resting on the bottom, respectively.
Figure 2B:
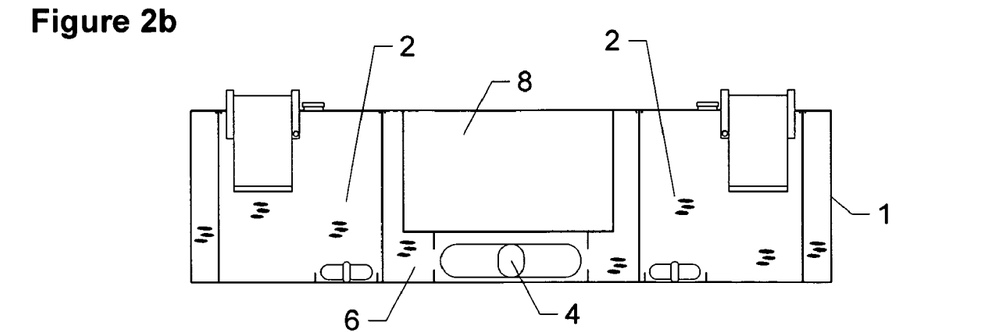

In the vertical sectional view in FIG. 2a a plate 1 may be seen having a central stirring system 4 that is supported by the structure; the figure shows the minibioreactors or wells 2 laterally surrounded by the thermostat bath 6, the central stirrer 4 and upper and lower accesses 8 through which heat exchange is supplied, as it will be disclosed further on, to the bath 6 and energy to the central stirrer 4.

In one variant shown in FIG. 2a, the stirring system 4 rests on the bottom of the plate 1, and there is only provided one upper access 8.

Figure 3A:
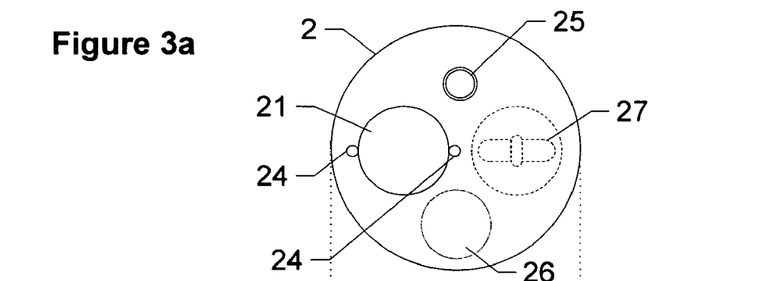
FIGS. 3a and 3b are plan and sectional views, respectively, of one of the wells or minibioreactors.
Figure 3B:
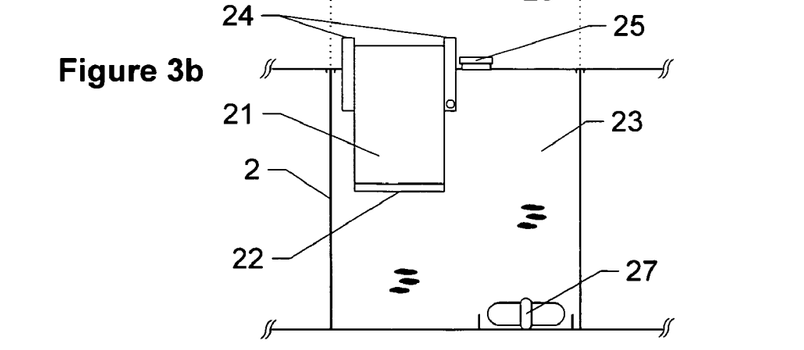

FIGS. 3a and 3b show in greater detail one of the wells or minibioreactors 2, in plan view and in vertical sectional view.

The minibioreactor 2 comprises an optical port 21, which allows carrying out measurements by transmission or reflection through its lower window 22, which is kept always immersed below the level of the liquid 23, thus providing an optical path which length is not level-dependent.

The minibioreactor 2 is likewise provided with gas inlet and outlet tubes 24, a septum 25 for filling, inoculating and eventually supplying and draining liquids, an initially not perforated optional port 26, which would allow non-optical probes or micro-probes to be added, and a rotor 27 of a magnetic stirrer.

In short, the plate accommodates, as stated, a certain number of minibioreactors (for example, six), said minibioreactors being each sealed to the environment, to the rest of the minibioreactors and to a bath permitting common thermostating thereof. The central symmetry geometrical arrangement of the wells inside the plate ensures, due to their design, that the overall temperature control may be carried out centrally, thus ensuring the thermal homogenization of each the minibioreactors. Each minibioreactor includes an individual stirring member for allowing homogenization of its contents. The energy required for imparting the movement to said element will be provided contactlessly from the outside. The minibioreactors will be further provided with access ports for gas inflow and outflow with the purpose of providing the culture with the suitable oxygen partial pressure as well as other gases as necessary. Sterility of said access will be ensured by filters connected to said ports. Filling, inoculation and, in case of being necessary, sample collection from minibioreactors will be carried out by a third port through a septum-type closure. For continuous or feedbatch processes said septum may be used for inserting cannulae for supplying and draining liquids throughout growth.

Culture parameter measurements will be carried out from the outside, without interfering the plate sterile barrier. Possible measuring methods contemplated herein are as follows:

optical access to the contents of each minibioreactor, from the walls thereof or from transparent portions therefrom.

electric access to the sensor or micro-sensor outer contacts provided inside the minibioreactors before the sterilization process.

measurements carried out from the outside on liquids subjected to ionic exchange with the bioreactor contents through membranes maintaining the sterile barrier.

The volume of the plate corresponding to the outside of the minibioreactors will be filled with a liquid (for example, water) not necessarily sterile. Stirring of such liquid will be imparted from the outside in a like manner to the stirring of the bioreactor contents. Heat will be supplied to or drained from said liquid, from the outside as well, for obtaining the thermal homogenization of the bath and the well contents.

The plate as a whole, or at the very least, a part thereof that will be in contact with the culture media, will be disposable and it will be presented, already sterilized, inside a bag or on compartments, with which it becomes a consumable product for the user. Its filling, inoculation, and connection to the filters does not require any other tool other than a laminar flow chamber and they are the only processes to be performed in a sterile area.

Description of the Support Device

A plate 1 as noted above fitted inside a device 3 is shown in FIGS. 4a and 4b in a vertical sectional view and in a plan view; this device has sub-systems supplying the plate (for delivering energy and heat on the plate, as well as measuring and control systems) and is, in turn, housed in an outer box 9.

The outer box 9 may accommodate the different parts of the device 3 and the plate 1 of minibioreactors 2, as well as a data control and acquisition system (not shown in FIGS. 4a, 4b), although this may be also located outside the box 9 and connected thereto by cables.

Figure 4A:
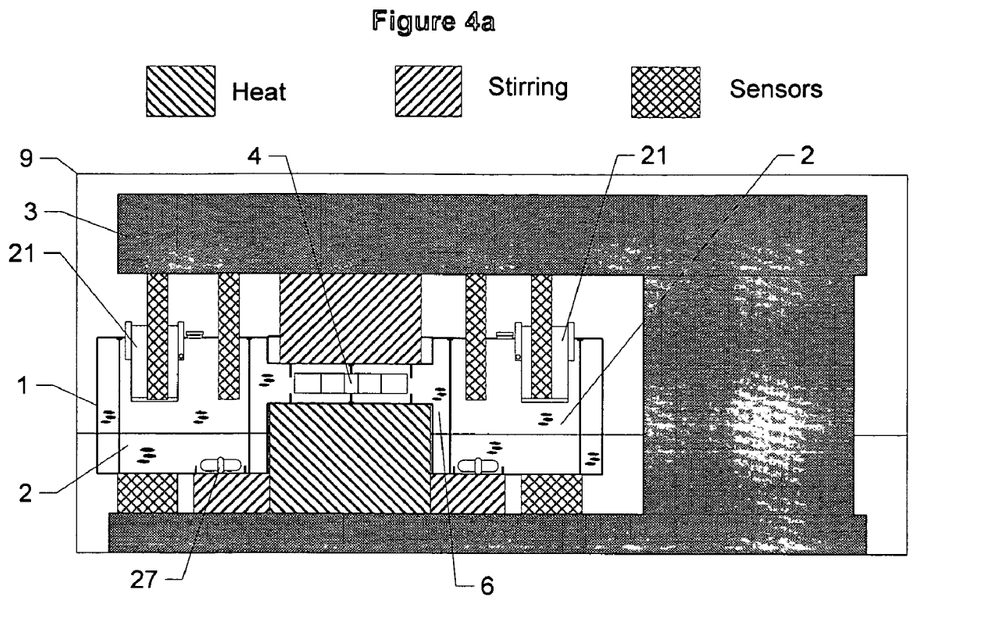
FIGS. 4a and 4b are vertical sectional (4a) and plan views, respectively, of a plate fitted inside a device according to one embodiment of the invention.
Figure 4B:
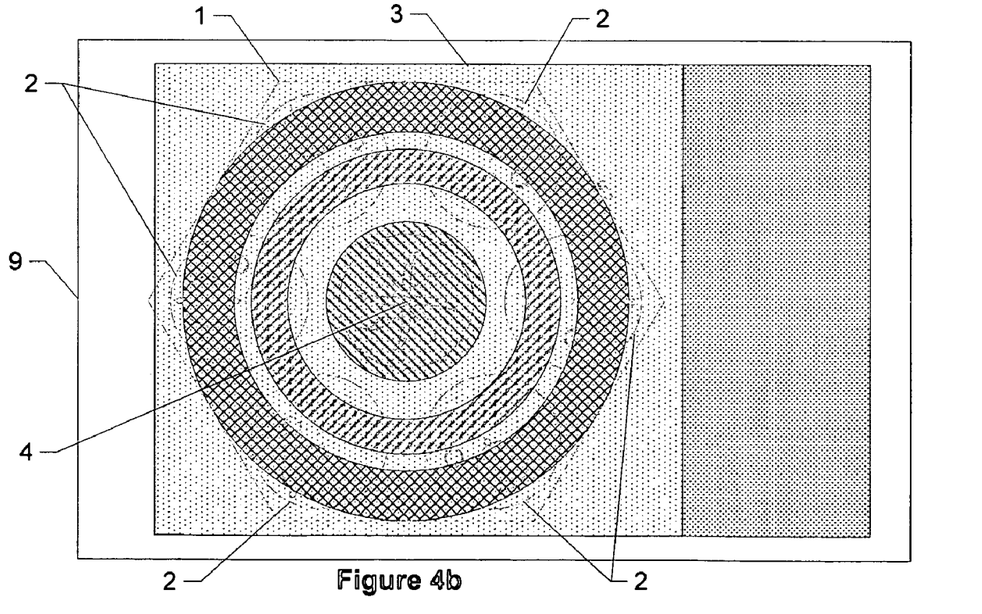

As the cover of the outer box 9 closes, alignment and connection of the different sub-systems in the plate 1 is facilitated.

The different shading patterns in FIGS. 4a, 4b allow the sub-systems of the device 3 to be identified which provide the heat exchange to the thermostat bath 6 of the plate 1 and the energy to the central stirrer 4 of said bath and to the stirrers 27 in each well 2, and to the optical sensors (lower part of the plate 1 and optical port 21) or other type of sensors of micro-sensors. FIG. 4b shows how the spacing of the different sub-systems in circular crowns is facilitated by the well central symmetry arrangement.

Figure 5A:
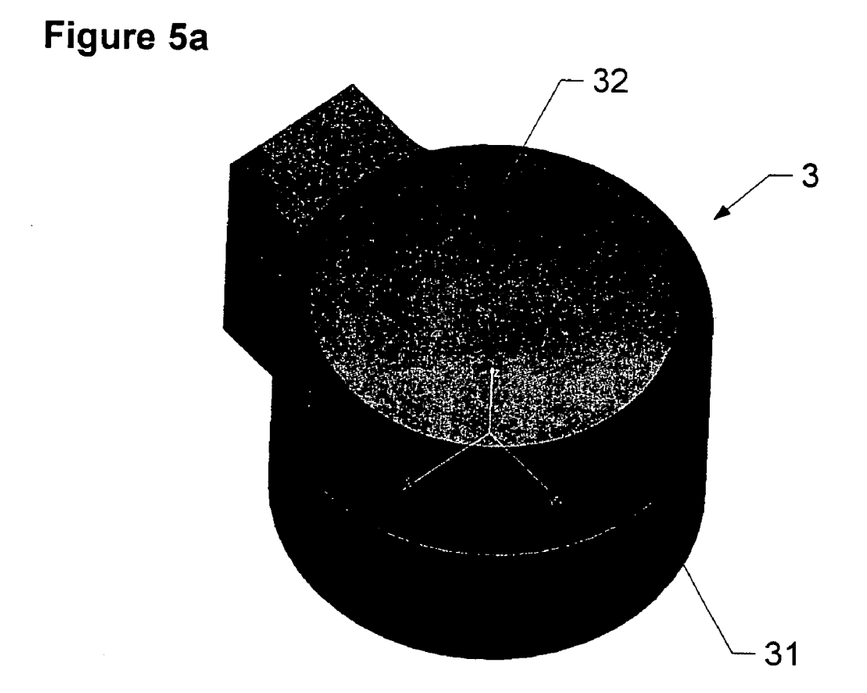
FIGS. 5a and 5b are perspective views of one embodiment of a device accommodating one plate, which has been depicted with the cover closed and without cover, respectively.

The outer shape of the device 3 is depicted, in a possible variant of one embodiment, in FIG. 5a: it comprises a base 31 in which a plate 1 is housed (FIG. 5b), that is closed by a cover 32.

Figure 6:
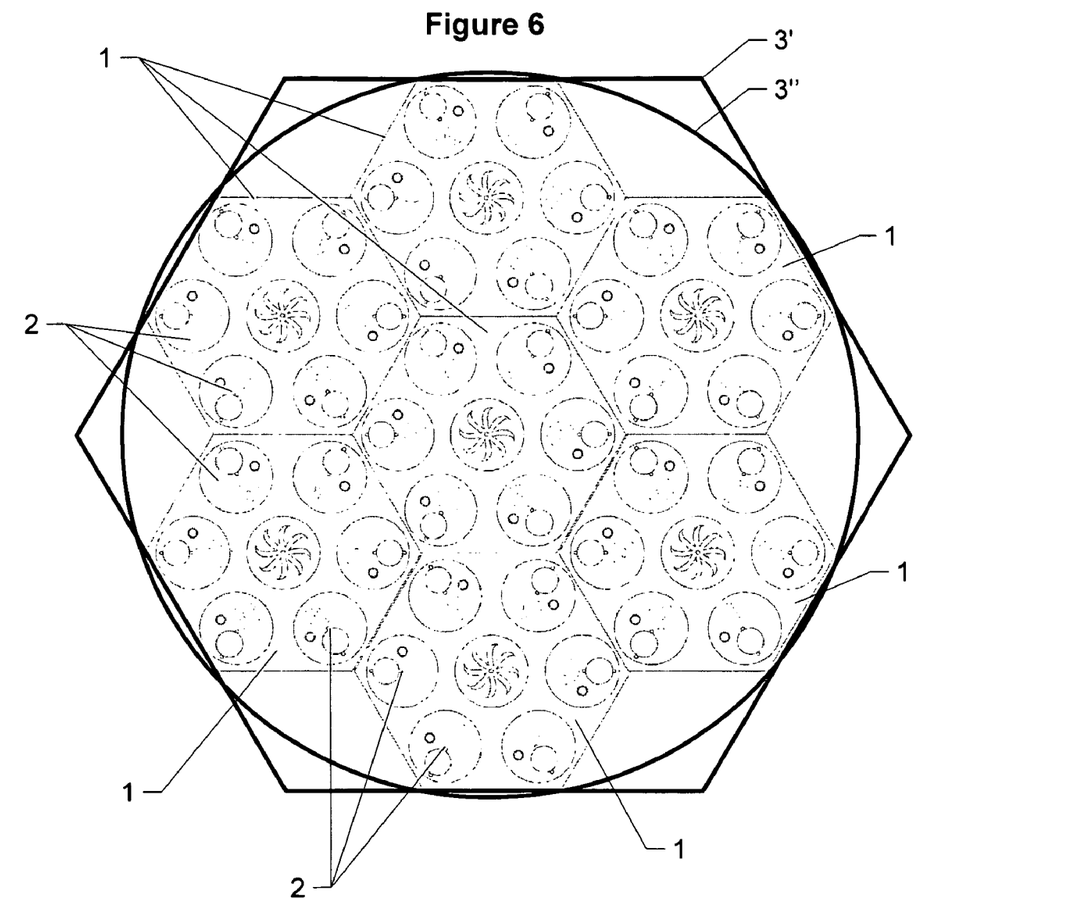
FIG. 6 shows a device according to a further embodiment of the invention accommodating seven plates, with forty-two minibioreactors altogether.

As it may be seen from the plan view of FIG. 6, a device may be also designed accommodating several plates 1 having a polygonal perimeter: the figure shows an arrangement of seven plates 1 (forty-two minibioreactors altogether) inside a single device. The device perimeter may be, in this case, hexagonal 3' or circular 3".

In general, providing m plates 1 having a polygonal perimeter each having n wells, macro-plates having n×m wells 2 may be thus formed.

Wells 2 in each plate 1 will be at the same temperature, so that the system allows obtaining m experiments at different temperatures each having n replicas.

Figure 5B:
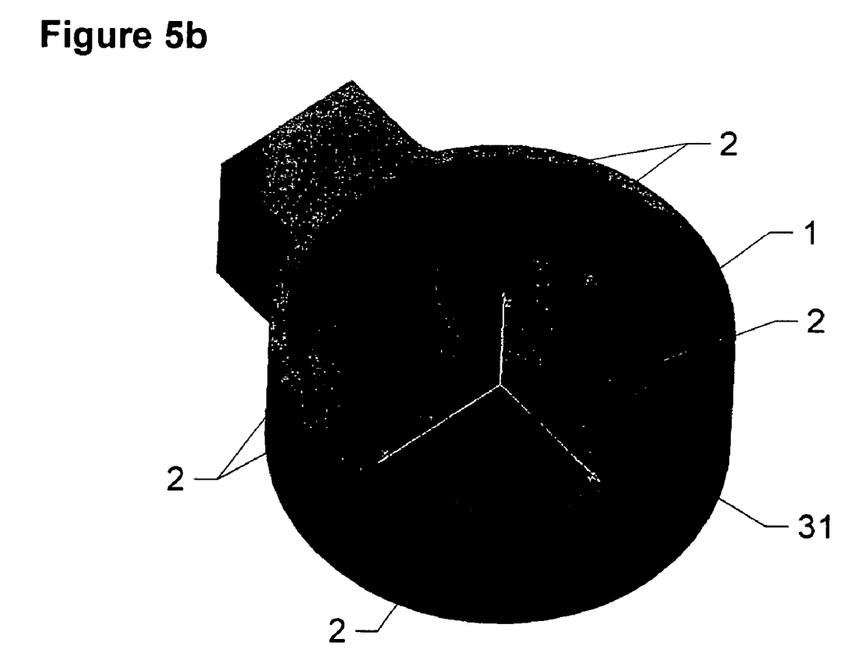
Figure 7A:
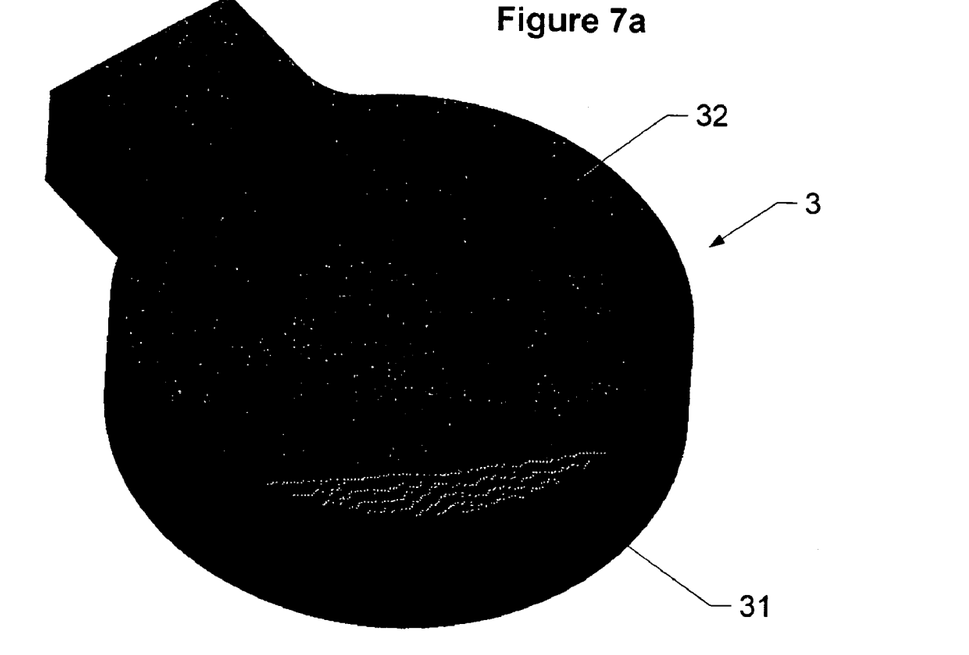
FIGS. 7a and 7b are analogous views to FIGS. 5a and 5b, for the device in FIG. 6.
Figure 7B:
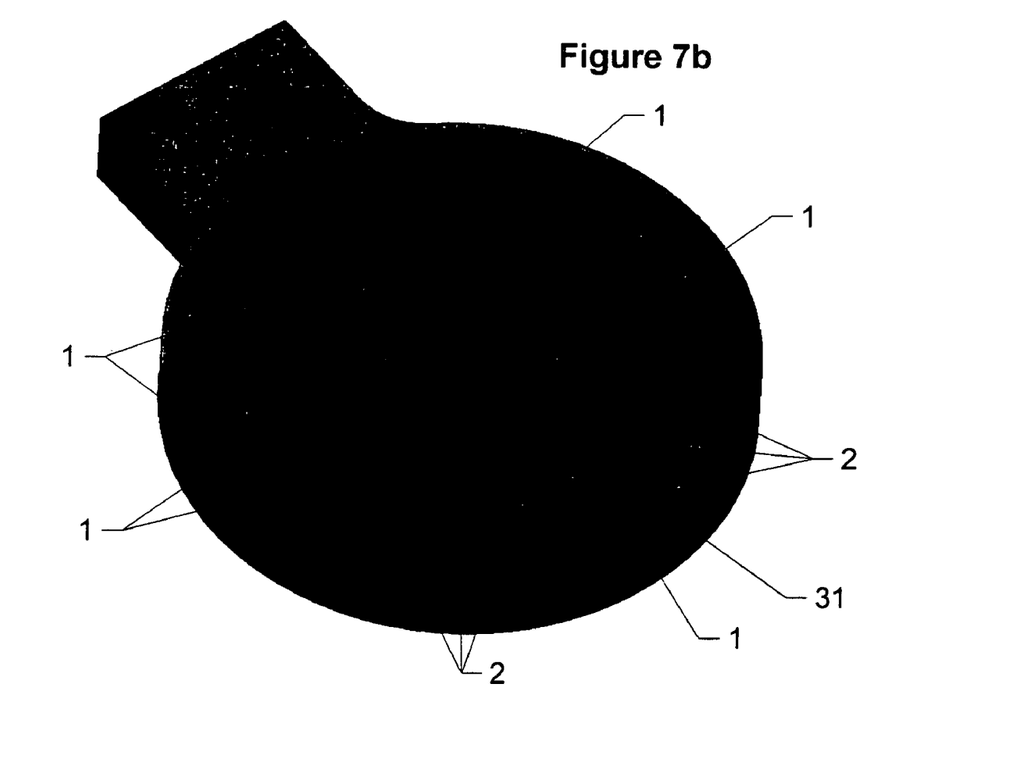

FIGS. 7a and 7b are analogous to FIGS. 5a and 5b, for one embodiment of the device 3 with seven plates 1 each having six wells 3.

In short, the outer measuring device or system will accommodate one or more plates therein, which will be fitted through the aperture of one or more portions of said device. Its functions will be as follows:

Controlled heat exchange with the bath thermostating the n minibioreactors simultaneously.

Energy transmission to the n individual stirrers.

Gas exchange through the sterile filters with culture aeration through the head or by means of a tube that penetrates inside the liquid. Aeration in each well will be able to be controlled separately.

Non-invasive monitoring and/or controlling of the culture parameters. By way of examples, pH, optical density (cell concentration) and oxygen dissolved separately in each well.

Possibility of supplying and draining of liquids.

Possibility of providing further probes and biosensors.

Possibility of system customization for specific applications.

Connection to a Control and Operating System

Figure 8A:
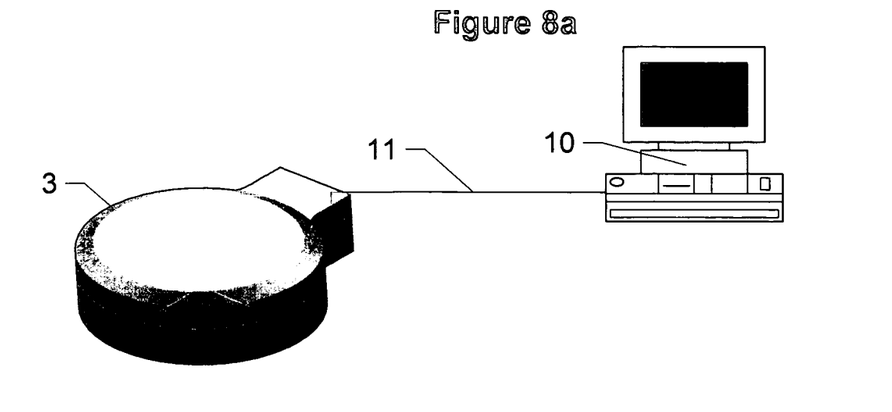
FIGS. 8a and 8b show wiring diagrams of the device to a computer and to a computer network, respectively.

In FIG. 8a, a device 3, containing a single plate or a set of m plates is connected to a computer or a control system 10 which will manage the subsystem setup and control parameters and collect the measurement data. The connection between both is carried out either by a cable 11 which is adapted to a data transmission standard protocol or by means of a custom-made connection which contemplates both data and signal transmission.

Figure 8B:
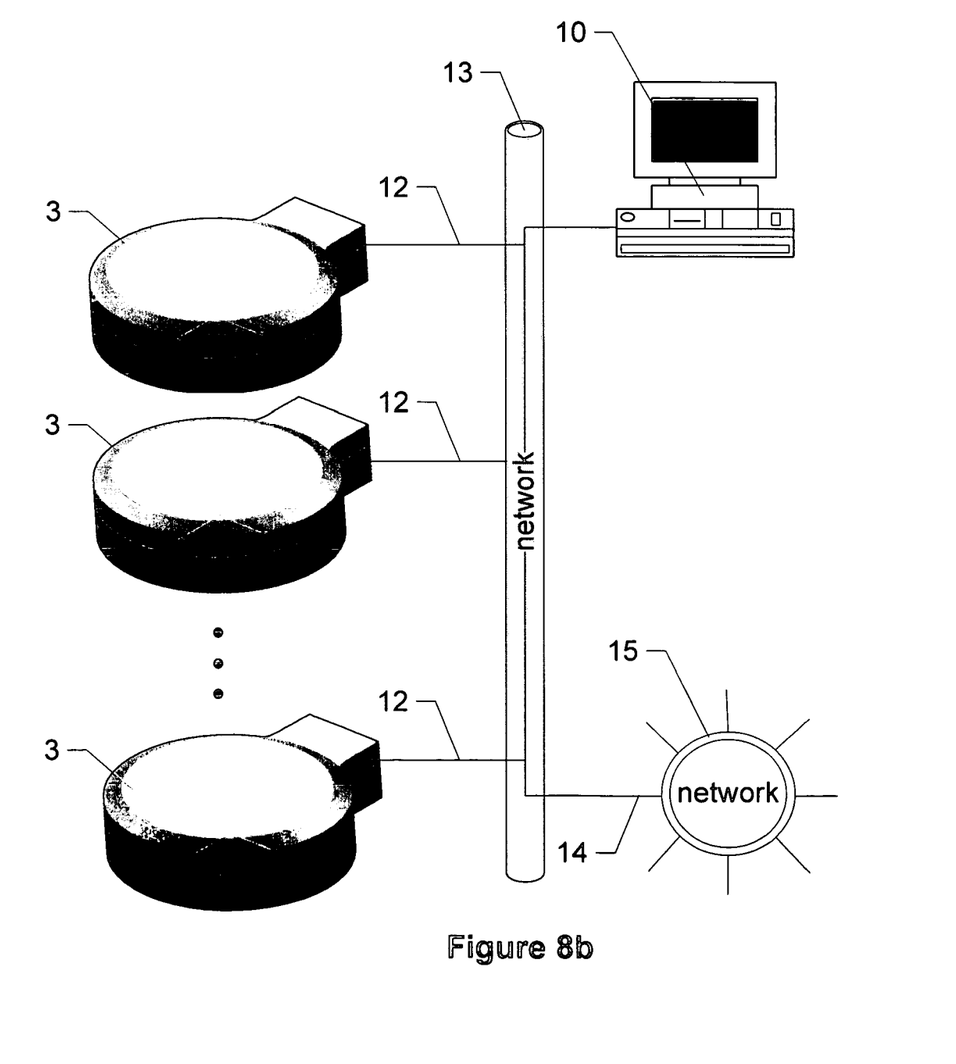

In FIG. 8b, a series of devices 3, containing any combination of plates or set of plates, is connected to a computer or control system 10 which will manage the setup and control parameters and collect the measurement data. The connection between both is carried out either by cables 12 connecting the systems to a data communication network 13, with the possibility of incorporating remote devices and/or computers through a connection 14 to an external network 15.

In short, the device will be able to be connected to a computer system, through a dedicated connection or through a data communication network. The control software will allow connection of a sufficient number of devices such that it provides automatic control capability on the large number of cultures necessary for the application of the HTS system.

The managing system of the whole bioreactor assembly would fix the control instructions of each unit and monitor the evolution of the parameters of each bioreactor and its response to the possible stimuli applied. The proposal then consists of the application of the capabilities and versatility of a device that comprises a battery of small volume minibioreactors made of plastic pieces and provided with micro-probes for simultaneously carrying out multiple tests in the development of biotechnological processes and products. One important aspect is that the device is of the modular type, that is, the plates comprising n minibioreactors will be able to be multiplied m times depending on the number of tests and the rate at which they have to be carried out in the final application.

The measurement of the biological and enzymatic activities themselves, created by genetic modifications or induced by different substances is thus of a great importance for informing and assessing the object being researched and establishing corresponding correlations regarding activities, properties and possibilities of application of the different exploitable substances or processes at industrial level. It is worth mentioning that the more relevant biological variables on which the culture tracking in the proposed device will be focused are the measurement of the cell concentration (by means of light absorption or refraction optical systems) and the measurement of the cell activity (from measurements of the oxygen consumption). The measuring system of both variables will allow keeping track of the response of the cultures at different varying conditions of the physicochemical environment of the organisms under culture and the disturbances therein by adding substances having physiological effects, either growth-enhancing effects or, on the contrary, with toxic effects for culture growth. Likewise, the system will also allow the possibility of keeping track of enzyme-catalyzed reactions, produced both by cells harvested in the system under different controlled conditions and enzymes or multi-enzymatic systems in in vitro conditions. In addition, the system will be able to include all those measuring and control elements necessary for culture growth in optimum conditions (pH, temperature, dissolved oxygen concentration, stirring, conductivity and osmolarity.

The invention claimed is:

1. A device for substantially simultaneously and automatically carrying out a plurality of biological cultures at small volumes and with controlled conditions similar to those which can be obtained with large scale bioreactors, the device comprising:
at least one plate which comprises a plurality of minibioreactors for culturing in sterile conditions, each minibioreactor being sealed to the environment, to the rest of the minibioreactors and to a common thermostat bath, each minibioreactor including an individual stirring member for providing homogenization of any contents of the minibioreactor, and one or more sterile access points enabling one or more of filling, inoculation, gas exchange, liquid exchange and parameter measurement; and
a support device intended for receiving the at least one plate therein, each of the at least one plates being fitted through the opening of at least one part of said support device, said support device comprising one or more means for controlled heat exchange with the thermostat bath, means for energy transmission to the individual stirring members, means for gas exchange through sterile filters and means for non-invasive monitoring and/or controlling of the culture parameters, said means for gas exchange and said means for monitoring and/or controlling the culture parameters each comprising individual probes and individual connections for each minibioreactor, which can be simultaneously engaged with said sterile access points of the minibioreactor.

2. A device as in claim 1, wherein each of the at least one plates further comprises a thermostat bath central stirrer.

3. A device as in claim 1, wherein the at least one plate comprises a number of individual minibioreactors in a polygonal arrangement, with a central area which facilitates common thermostating of said minibioreactors.

4. A device as in claim 1, wherein the device is connected to a computer system, either via a dedicated connection or through a data communication network.

5. A device as in claim 1, wherein each minibioreactor comprises an upper cover having an optical port including a tube that penetrates within the minibioreactor so that its lower end is immersed into a liquid contained in said minibioreactor.

6. A device as in claim 5, wherein an optical sensor and light source is placed in the optical port, at the bottom portion of the plate facing said optical port and/or on the lateral surface of the reservoir.

7. A device as in claim 5, wherein an optical fiber or light guide is placed in the optical port, at the bottom portion of the plate facing said optical port and/or on the lateral surface of the reservoir.

8. A device as in claim 5, wherein an additional port is fitted through the upper cover so that the end of said port is immersed into the liquid, said end being provided with a filter or semi-permeable membrane.

9. A device as in claim 5, wherein an additional port is fitted through the upper cover so that the end of said port is immersed into the liquid, said end containing a sensor or microsensor.

10. A device as in claim 1, wherein heat exchange between the support device and the thermostat bath of the plate is carried out by one or more of by means of a heating resistance that is in contact with a portion of the plate outer surface; by means of a Peltier cell that is in contact with a portion of the plate outer surface; by means of a heating resistance that is immersed into said bath; and by radio frequency heating performed from the outside.

11. A device as in claim 1 further comprising a temperature probe immersed into one of the thermostat bath and the contents of one or more of the minibioreactors.

12. A device as in claim 1 further comprising an additional minibioreactor surrounded by the thermostat bath, in which a temperature probe is immersed.

13. A device as in claim 1 further comprising a stator located below each individual stirring member, for energy transmission to each said stirring member.

14. A device as in claim 1 further comprising a rotating magnet located below one or more of the individual stirring members, for energy transmission to each respective stirring member, each said magnet being rotated by one of a mechanical driving system actuated by a common electric motor and a respective individual electric motor.

15. A device as in claim 2 further comprising a stator or a rotating magnet located below the thermostat bath central stirrer, for energy transmission to said stirrer.

16. A device as in claim 2 further comprising means for causing the common thermostat bath stirrer to be rotated from a drive providing controlled sequencing of the minibioreactors.

17. A device as in claim 1 wherein each minibioreactor has a volume ranging from 5 to 25 ml.

18. A device as in claim 1 wherein the plate is at least in part disposable.

19. A device as in claim 1 wherein the plate is formed of a base made of plastic material and at least one cover made of plastic material or other transparent material.

20. A method for substantially simultaneously and automatically carrying out a number of biological cultures at small volumes and with controlled conditions similar to those which can be obtained with large scale bioreactors, the method comprising:
carrying out cultures in sterile conditions in a number of minibioreactors provided in a plate, each of said minibioreactors being sealed to the environment, to the rest of the minibioreactors and to a common thermostat bath, and each minibioreactor including an individual stirring member for allowing homogenization of its contents, and one or more sterile access points enabling one or more of filling, inoculation, gas exchange, liquid exchange and parameter measurement;

fitting at least one plate into a support device which comprises one or more of means for controlled heat exchange with the thermostat bath, means for energy transmission to the individual stirring members, means for gas exchange through sterile filters and means for non-invasive monitoring and/or controlling of the culture parameters, said means for gas exchange and for monitoring or controlling of the culture parameters comprising individual probes and connections for each minibioreactor, which can be simultaneously engaged with said sterile access points of the minibioreactor; and non-invasive monitoring and/or controlling of the culture parameters.

\* \* \* \* \*